US006254894B1

(12) United States Patent
Denkewicz, Jr. et al.

(10) Patent No.: US 6,254,894 B1
(45) Date of Patent: *Jul. 3, 2001

(54) SILVER SELF-REGULATING WATER PURIFICATION COMPOSITIONS AND METHODS

(75) Inventors: Raymond P. Denkewicz, Jr., Warwick; John D. Rafter, Providence; Mark A. Bollinger; Joseph W. Grenier, both of Warwick; Therese R. Souza, Cranston, all of RI (US)

(73) Assignee: Zodiac Pool Care, Inc., Smithfield, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/349,826

(22) Filed: Jul. 8, 1999

Related U.S. Application Data

(60) Continuation-in-part of application No. 09/028,599, filed on Feb. 24, 1998, now Pat. No. 5,935,609, which is a division of application No. 08/628,405, filed on Apr. 5, 1996, now Pat. No. 5,772,896.

(51) Int. Cl.$^7$ .................. A01N 59/16; A01N 59/06; B01D 17/06; C02F 1/68
(52) U.S. Cl. ............... 424/618; 424/682; 210/748; 210/749; 210/764
(58) Field of Search ................. 424/618, 682

(56) References Cited

U.S. PATENT DOCUMENTS

| | | | |
|---|---|---|---|
| 553,383 | 1/1896 | Bailey | 204/76 |
| 1,473,331 | 11/1923 | Bechhold | 210/266 |
| 1,642,089 | 9/1927 | Schreier | 210/761 |
| 2,008,131 | 7/1935 | Dieck et al. | 424/72 |
| 2,434,190 | 1/1948 | Barnes et al. | 424/16 |
| 3,268,444 | 8/1966 | Renn | 210/638 |
| 3,788,982 | 1/1974 | Zsoldos, Jr. et al. | 502/350 |
| 3,823,088 | 7/1974 | Box, Jr. et al. | 210/764 |
| 3,883,442 | 5/1975 | McArthur | 210/760 |
| 3,950,253 | 4/1976 | Stern | 210/18 |
| 4,043,932 | 8/1977 | Fresenius et al. | 210/668 |
| 4,092,245 | 5/1978 | Franks et al. | 424/16 |
| 4,147,665 | 4/1979 | Ikari et al. | 210/510 |
| 4,173,549 | 11/1979 | Fein et al. | 252/463 |
| 4,309,992 | 1/1982 | Dodak et al. | 204/152 |
| 4,361,486 | 11/1982 | Hou et al. | 210/772 |
| 4,381,998 | 5/1983 | Roberts et al. | 210/503 |
| 4,389,311 | 6/1983 | La Freniere | 210/198 |
| 4,396,512 | 8/1983 | Beauman et al. | 210/668 |
| 4,492,618 | 1/1985 | Eder | 204/152 |
| 4,504,387 | 3/1985 | LeMire et al. | 210/101 |
| 4,608,247 | 8/1986 | Heinig, Jr. | 424/16 |
| 4,695,379 | 9/1987 | Nohren, Jr. et al. | 210/282 |
| 4,787,973 | 11/1988 | Ando et al. | 210/282 |
| 4,923,619 | 5/1990 | Legros | 210/764 |
| 4,935,116 | 6/1990 | LeMire | 204/237 |
| 5,017,295 | 5/1991 | Antelman | 210/764 |
| 5,045,195 | 9/1991 | Spangrud et al. | 210/266 |
| 5,089,275 | 2/1992 | Antelman | 424/602 |
| 5,098,582 | 3/1992 | Antelman | 210/759 |
| 5,128,036 | 7/1992 | Svensson | 210/264 |
| 5,135,654 | 8/1992 | Heskett | 210/638 |
| 5,149,354 | 9/1992 | Delaney | 71/67 |
| 5,178,768 | 1/1993 | White, Jr. | 210/663 |
| 5,183,496 | 2/1993 | Blenk et al. | 210/668 |
| 5,192,452 | 3/1993 | Mitsui et al. | 210/760 |
| 5,198,118 | 3/1993 | Heskett | 210/638 |
| 5,215,659 | 6/1993 | Ando | 210/282 |
| 5,221,484 | 6/1993 | Goldsmith et al. | 210/650 |
| 5,223,149 | 6/1993 | Antelman | 210/764 |
| 5,256,616 | 10/1993 | Heller et al. | 502/350 |
| 5,258,108 | 11/1993 | Cassidy | 204/150 |
| 5,266,207 | 11/1993 | Boye et al. | 210/653 |

(List continued on next page.)

FOREIGN PATENT DOCUMENTS

| | | |
|---|---|---|
| 0 128 782 A1 | 12/1984 | (EP) . |
| 128782 A1 | 12/1984 | (EP) . |
| 150559 A2 | 8/1985 | (EP) . |
| 399658 A2 | 11/1990 | (EP) . |
| 684210 A1 | 11/1995 | (EP) . |
| 2688133 * | 9/1993 | (FR) . |
| 85008072 * | 2/1985 | (JP) . |
| 60-183086 | 9/1985 | (JP) . |
| 5271029 | 10/1993 | (JP) . |
| 6226262 | 8/1994 | (JP) . |
| 07017803 * | 1/1995 | (JP) . |
| 07118114 | 5/1995 | (JP) . |
| 7133201 | 5/1995 | (JP) . |
| 07158299 | 6/1995 | (JP) . |
| 07303809 | 11/1995 | (JP) . |
| WO 96/14093 | 5/1996 | (WO) . |
| WO 97/37939 | 10/1997 | (WO) . |

OTHER PUBLICATIONS

Pedahzur, et al., "The Interaction of Silver Ions and Hydrogen Peroxide in the Inactivation of E. Coli: A Preliminary Evaluation of a New Long Acting Residual Drinking Water Disinfectant," *Wat. Sci. Tech.*, 31(5–6):123–129 (1995).

Ullmann's Encyclopedia of Industrial Chemistry, Fifth, Completely Revised Edition, Vol. A24, paragraph 13.2 "Bactericidal (Oligodynamic) Effect," pp. 160–161 (undated) (Editors: Barbara Elvers, Stephen Hawkins, William Russey, Gail Schulz)*.

FOSS Wasser Abwasser Abfall Encyclopedia, p. 108 (Lexikron von a bis z—Karl Kramer Verlag Stuttgart (1980)*.

CRC Handbook of Chemistry and Physics, 63rd Ed., p. B–38, CRC Press Inc., (1982)*.

International Preliminary Examination Report in PCT/US97/05655*.

International Search Report in PCT/US97/05655*.

*Primary Examiner*—S. Mark Clardy
*Assistant Examiner*—Alton Pryor
(74) *Attorney, Agent, or Firm*—Bruce D. Gray; Dean W. Russell; Kilpatrick Stockton LLP

(57) ABSTRACT

The present invention relates to water purification compositions comprising silver and a second material, such as aluminum or zinc metal, to methods of treating or purifying water using this composition.

25 Claims, No Drawings

U.S. PATENT DOCUMENTS

| | | | |
|---|---|---|---|
| 5,279,748 | 1/1994 | Hackett | 210/757 |
| 5,336,499 | 8/1994 | Antelman | 424/405 |
| 5,342,528 | 8/1994 | Adachi et al. | 210/668 |
| 5,352,369 | 10/1994 | Heinig, Jr. | 210/760 |
| 5,510,550 * | 4/1996 | Cheung et al. | 585/259 |
| 5,518,613 | 5/1996 | Koczur et al. | 210/266 |
| 5,531,908 | 7/1996 | Matsumoto et al. | 210/760 |
| 5,543,046 | 8/1996 | Van Rijn | 210/490 |
| 5,772,896 | 6/1998 | Denkewicz, Jr. et al. | 210/754 |
| 5,935,609 * | 8/1999 | Denkewicz et al. | 424/618 |

* cited by examiner

SILVER SELF-REGULATING WATER PURIFICATION COMPOSITIONS AND METHODS

CROSS-REFERENCE TO RELATED APPLICATIONS

This is a continuation-in-part of U.S. application Ser. No. 09/028,599, filed Feb. 24, 1998, now U.S. Pat. No. 5,935,609 which in turn, is a divisional of U.S. application Ser. No. 08/628,405, filed Apr. 5, 1996, now U.S. Pat. No. 5,772,896, he entire contents of each of which are hereby incorporated by reference.

BACKGROUND OF THE INVENTION

1. Field of the Invention

The present invention relates to compositions and methods for treating water, and in particular, compositions containing silver and a material such as aluminum or zinc.

2. Description of the Related Art

In many situations, water is purified to remove microorganisms, such as bacteria or algae, and harmful metal ions, such as mercury, lead and copper. Water purification may be accomplished by filtration, providing water suitable for consumption or for use in recirculating systems such as swimming pools, hot tubs, spas and cooling towers. Water purification may also be accomplished by adding chemicals like chlorine or bromine. However, it has been found that not only does chlorine have an objectionable odor, but that it can also cause skin irritations and serious eye irritations to bathers in pools or spas.

Because of the objectionable physical properties of chlorine a number of alternate water treatment systems which operate without chlorine have been developed in recent years. One of the most effective types of alternative water treatment systems is a system in which silver ions are added to water to kill microorganisms therein. However, it has been found that in many cases systems of this type are only partially effective due to insufficient control of the silver ion levels, which should be maintained between about 0.01 ppm and about 0.1 ppm. Failure to maintain this ion level concentration may result in staining or health problems.

Accordingly, a water purification composition that provides better control of the silver ion levels will provide an improvement over conventional silver-containing water purification compositions by avoiding or reducing the effect of disadvantages as noted above.

SUMMARY OF THE INVENTION

In one aspect, the invention features a water purification composition including silver and aluminum metal. The silver may be present as metallic silver or silver compounds, such as soluble or sparingly soluble silver salts. These salts can include silver nitrate or silver chloride.

In another aspect, the invention features a water purification composition including silver, and metallic zinc and aluminum. In a particular embodiment of this aspect of the invention, the silver is in metallic form, and in an even more particular embodiment, the zinc and aluminum are present as an alloy. Examples of these alloys include about 2 to about 5 weight percent aluminum, and respectively, about 98 to about 95 weight percent zinc, or alternatively, about 2 to about 5 weight percent zinc, and respectively, about 98 to about 95 weight percent aluminum.

In a further aspect, the invention features a water purification composition including silver as a biocidal element and zinc metal. In addition, the water purification composition may further include aluminum or copper.

In yet another aspect, the invention features a method of purifying water by exposing the water to one or more of the water purification compositions described above. In a particular embodiment, the water purification system provides a concentration of silver in the water desirably between about 0.01 and about 0.1 ppm.

In still another aspect, the invention features a water purification system including silver and aluminum metal and an oxidizing agent or source of an oxidizing agent. The oxidizing agent can be selected from the group consisting of free available chlorine, ozone, and chlorine dioxide. In addition, the source of oxidizing agent can be selected from the group consisting of dipersulfates, monopersulfates, hypochlorite salts, chlorites, peroxides, perchlorates, hypobromites, percarbonates, chlorine dioxide and permanganates.

The water purification composition of the present invention can provide a number of advantages. Because the silver ion concentration in the body of water is controlled by equilibrium reactions, the effectiveness of the composition is not dependent on flow rate. Therefore, there is no need to add filler material to inhibit particle erosion at high flow rates, and a device containing the purification composition can be used directly in high flow conditions, such as in spa filter cores, without requiring modification of the plumbing system to control flow rates through the device.

In addition, the water purification composition of the invention imparts and maintains sufficient amounts of silver ions in water to effectively disinfect the water while reducing the concentration of other undesirable metal ions in the water, but without exceeding the levels of silver that cause staining or health problems.

When the water purification composition of the invention contains silver and zinc metal, the composition releases and maintains a residual concentration of zinc ions which provides algaestatic properties. Furthermore, metallic zinc helps remove hazardous metal ions (e.g., mercury, lead) and metal ions which are known to stain pool and spa surfaces (e.g., iron, copper, manganese) effectively.

When the water purification composition of the invention contains silver and aluminum metal, the aluminum ions released into the water can act as a flocculating agent to aid in the removal of particulates and/or metals. Furthermore, the aluminum metal may be present as an alloy with other metals, such as zinc or copper, that provide other properties to the composition, such as microbiocidal or algaestatic properties. An inorganic oxide, if present, which has a slightly positive, zero, or negative surface charge, also assists in the adsorption of hazardous metal ions.

The water purification composition of the invention does not significantly alter the pH, calcium hardness, or free available chlorine in the water. It can be used in swimming pools and spas where elevated pH reduces the effectiveness of chlorine, calcium hardness must be maintained to prevent corrosion, and chlorine residuals must be maintained for disinfection.

Other advantages and features of the invention will be apparent from the description of specific embodiments of the invention, and from the claims.

DESCRIPTION OF SPECIFIC EMBODIMENTS OF THE INVENTION

The term "zeta potential" as used herein, means surface charge. The zeta potential of an inorganic oxide can be determined, for example, by measuring electrophoretic mobility.

The phrase "point of zero charge," as used herein, means the pH at which the surface charge of the inorganic oxide (i.e., zeta potential) is zero.

The term "$E_h$," as used herein, means the reduction potential with respect to the standard hydrogen electrode.

The term "recirculated," as used herein, means continuous flow of the water to expose the water to the water purification device, for example, in cooling towers, spas, swimming pools, and hot tubs.

In one embodiment, a water purification composition includes silver and a second material, which is desirably a metal. The silver may be in metallic form or present as a compound, such as soluble or sparingly soluble silver salts. Examples of these salts can include silver nitrate and silver chloride. Examples of the second material can include zinc, copper, aluminum, iron, or manganese and can have an $E_h$ less than about 0.34 V. In a particular aspect of this embodiment, this second material is zinc or aluminum metal. Furthermore, the second material may be homogenous or heterogeneous, e.g., an alloy of two or more metals. A particular heterogeneous material suitable for use in the present invention is an alloy of aluminum and zinc. Examples of these alloys can include about 2 to about 5 weight percent aluminum, and respectively, about 98 to about 95 weight percent zinc, or alternatively, about 2 to about 5 weight percent zinc, and respectively, about 98 to about 95 weight percent aluminum. The second material may be in the form of a powder, shavings, turnings, or larger pieces.

The silver content of the water purification composition is generally any amount that will provide a suitable silver ion concentration in the water when the composition is used. For most applications, a silver content between about 0.1 and about 10 weight percent, and more particularly between about 0.5 and about 5 weight percent, based upon the weight of the water purification composition, can be used. The second material, such as metallic zinc, metallic aluminum, or alloys thereof, may be included in the purification composition in amounts between about 2 and about 95 weight percent of the purification composition. More particularly, the second material may be included in the water purification composition in amounts between about 20 and about 80 weight percent of the water purification composition. More particularly still, the second material may be included in the purification composition in amounts between about 30 and about 70 weight percent of the purification composition.

The water purification composition may optionally further include an inorganic oxide. The inorganic oxide may have a point of zero charge between about 4 and about 9. Examples of such inorganic oxides include alumina, zeolites, silica, and titania. Alumina is particularly suitable. In particular, an alumina that is basic (i.e. has a zeta potential less than zero) and that has a surface area of at least about 0.5 $m^2/g$, and more desirably between about 50 $m^2/g$ and about 300 $m^2/g$ can be used. Alternatively, any inorganic oxides having a zeta potential of less than about +20 mV at the pH of the water being purified can be used.

In one embodiment, the silver is chemically deposited on the surface of the alumina support medium by known methods. For example, the silver can be deposited by the methods described in U.S. Pat. No. 5,352,369, which is incorporated herein by reference. In addition to classical impregnation techniques, silver can be deposited onto the support medium via chemical vapor deposition, ion exchange, electroplating methods, or coprecipitation. It is desirable that if the material is in bulk metallic form, such as metallic zinc or aluminum, it be mixed thoroughly with the silver coated alumina. Alternatively, the second material may be incorporated or deposited on the inorganic oxide with the silver.

Once deposited on the alumina, the silver may be reduced to its elemental state (if metallic silver is desired), for example, by heating the alumina containing the deposited silver in a reducing atmosphere (e.g., $N_2$, $H_2$, $NH_3$, or mixtures thereof, such as $N_2$ and $NH_3$) to a temperature between approximately 300° C. and 1050° C. Alternatively, the silver can be exposed to solutions containing chemical reducing agents, e.g., dextrose, glucose, sucrose, fructose, or hydrazine, to reduce the silver to the metallic state. Exposure to ultraviolet light or microwave radiation can also be used to reduce the silver.

Water purification materials containing between about 5 and about 98 percent by weight, and more desirably between about 20 and about 80 percent by weight, of silver-coated alumina can be used in water purification systems and methods according to the present invention.

In general use, the purification composition purifies water upon exposure to and subsequent mixing with water. In one embodiment, water is purified as it flows through a device containing the purification composition. Alternatively, the water can exchange into and out of a device containing the purification composition. The water purification composition desirably establishes an equilibrium silver ion concentration in the range of about 0.01 to about 0.1 ppm, and more desirably in the range of about 0.01 and about 0.05 ppm, in the water that is exposed to the purification composition. The silver ions kill bacteria and other microorganisms living in the water. In a particular embodiment, the water purification material can be used in the presence of oxidizing agents dissolved in the water, such as, for example, ozone, chlorine dioxide, or free available chlorine. Alternatively, the water purification material can be combined with a source of an oxidizing agent, such as, for example, dipersulfates, monopersulfates, hypochlorite salts, chlorites, peroxides, perchlorates, hypobromites, percarbonates, chlorine dioxide and permanganates.

The water purification composition effectively removes metal ions, such as mercury, lead, cadmium, iron, manganese, copper, nickel, chromium, barium, and arsenate. When the second material contains zinc, zinc ions are released into the water which provide algaestatic properties. When the second material is aluminum, the aluminum ions released into the water form a flocculant, particularly when the water is at a pH from about 5 to about 9. At this pH range, the aluminum ions form the flocculant $Al(OH)_3$. The water purification device does not significantly affect pH, calcium hardness, or free available chlorine in the water. Further advantages are obtained using the embodiment of the present invention wherein the silver is deposited on an inorganic oxide. The charged surface of the inorganic oxide can help maintain the silver ion concentration in the water and remove hazardous metal ions.

Because the silver ion concentration in the water is controlled by equilibrium reactions, this method of water purification is essentially flow rate independent. Generally, flow rates through a device containing the water purification composition desirably are between about 0.01 and about 3 gallons per minute per gram of purification composition. As an alternative to flowing over the water purification composition, the water may exchange into and out of a device containing the purification composition.

Furthermore, the water can recirculate through a water purification device that contains the water purification composition. For example, the water purification device may be used to treat high flow rate recirculating water systems such as spas, hot tubs, swimming pools and cooling towers. The device and water purification composition are also suitable for purifying drinking water. It is often desirable to locate the water purification composition so that it receives filtered water. For example, the water purification composition can be located in the core of a filter.

While not wishing to be bound by theory, the advantageous results of the present invention may be explained by one of the following theories. The first theory is that the equilibrium silver ion concentration in the water is maintained by equilibrium reactions between: (1) the silver metal and oxidizing agents dissolved in the water; (2) silver ions dissolved in the water and the second material; and (3) silver ions dissolved in the water and the inorganic oxide support medium. The second material appears to play a key role in maintaining the equilibrium silver ion concentration in the water. When the second material has an Eh less than 0.34 V, the silver ion concentration is maintained below 0.1 ppm, according to the Nernst equation (equation 1):

$$E = E^0 - \frac{RT}{nF} \ln Q$$

where R is the gas constant (8.314 J/(K mol)), T is temperature (K), n is the number of electrons, F is the Faraday constant ($9.648 \times 10^4$ C/mol), Q is the reaction quotient, $E^0$ is the standard cell electromotive force (emf), and E is the cell emf. Fundamentally, the key half-reaction may be:

$Ag^+ + e^- \rightarrow Ag^0$ $Eh = E^0 = 0.80V$

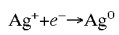

According to equation 1, in order to maintain a silver ion concentration ([Ag+]) of approximately 0.01 ppm at room temperature, E is about 0.38 V. This means that a reductant with Eh of around 0.38 V will maintain an equilibrium concentration of silver ions in water of around 0.01 ppm. The actual situation is affected somewhat by the other equilibria (e.g., silver metal with oxidizing agents), although the general principles apply.

Another theory is that the silver metal reacts with an oxidizing agent, such as chlorine, disassociating into ionic silver in the water. It is believed that the second material, such as zinc, copper, or aluminum, regulates this disassociation, possibly through involvement in other equilibrium reactions in the system.

The following Examples describe the preparation and testing of the purification material.

EXAMPLE 1

A new, 350 gallon spa was filled with balanced tap water (pH=8.36, total alkalinity=80 mg/L, calcium hardness=100 mg/L as $CaCO_3$, temperature=40° C., [$Ag^+$]<0.01 mg/L, [$Zn^{2+}$]<0.01 mg/L, [$Cl^-$]=60 mg/L). A cartridge containing 50 g of 2 wt % $Ag/Al_2O_3$ and 50 g Zn shot(2–14 mesh) was placed into the core of the spa filter. The cartridge was exposed to flow rates which ranged from 0 to 2 gallons per minute per gram of purification material. After 6 days of operation at 1–3 mg/L monopersulfate in chlorine equivalent units, the following parameters were recorded: pH=8.04, total alkalinity=80 mg/L, calcium hardness=100 mg/L as $CaCO_3$, [$Ag^+$]=0.043 mg/L, [$Zn^{2+}$]=0.03 mg/L. The system maintains low concentrations of $Ag^+$ and $Zn^{2+}$ ions in the water while not significantly affecting the total alkalinity, calcium hardness, or pH of the water.

EXAMPLE 2

A 350 gallon spa containing a cartridge with 50 g of 2 wt % $Ag/Al_2O_3$ and 50 g of Zn shot (2–14 mesh) inside the core of the filter and operating with balanced tap water (pH=8.01, total alkalinity=100 mg/L, calcium hardness=100 mg/L as $CaCO_3$, temperature=40° C., [$Ag^+$]=0.08 mg/L, [$Zn^{2+}$]=0.16 mg/L) was subjected to bather activity. Flow through the system ranged from 0 to 2 gallons per minute per gram of purification material. Five days each week, the spa was subjected to two bathers for a period of 20 minutes. Samples were analyzed for heterotrophic plate counts immediately before and 30 minutes after each bathing period. The monopersulfate level in chlorine equivalent units was approximately 1 ppm at the beginning of each bathing period. The detected bacteria levels are listed in Table I, where CFU denotes colony forming units.

TABLE I

| Day | CFU/mL Before Bathing | CFU/mL After Bathing |
|---|---|---|
| 1 | <1 | <1 |
| 2 | <1 | <1 |
| 3 | <1 | <1 |
| 4 | <1 | <1 |
| 7 | <1 | <1 |
| 8 | <1 | <1 |
| 9 | <1 | <1 |
| 10 | <1 | <1 |
| 11 | <1 | <1 |

EXAMPLE 3

A 350 gallon spa containing a cartridge with 50 g of 2 wt % $Ag/Al_2O_3$ and 50 g of Zn shot (2–14 mesh) inside the core of a spa filter was operated for 2 months with spa use (5 bather-hours/week). Flow rates through the system varied from 0 to 2 gallons per minute per gram of purification material. After this time, silver and zinc ion levels were measured to be 0.04 mg/L and 0.05 mg/L, respectively. Heterotrophic plate counts taken before and after bathing periods over four consecutive days all showed less than 2 CFU/mL. Monopersulfate levels were maintained at approximately 6 ppm (in chlorine equivalent units) during bathing periods when the samples were collected.

EXAMPLE 4

A 350 gallon spa containing a cartridge with 50 g of 2 wt % $Ag/Al_2O_3$ and 50 g Zn shot (2–14 mesh) inside the core of the filter was operated with balanced tap water (pH=7.93, total alkalinity=80 mg/L, calcium hardness=210 mg/L as $CaCO_3$, [$Ag^+$]=0.015 mg/L, [$Zn^{2+}$]=0.07 mg/L, [$Cl^-$]=180 mg/L) and with 20 hours/day of ozonation. Flow rates through the system varied from 0 to 2 gallons per minute per gram of purification material. Over a three week period, samples were collected for heterotrophic plate counts immediately before and 30 minutes after bathing activity. The bather demand corresponded to 7 bather-hours/week and monopersulfate levels (measured in chlorine equivalent units) ranged from 0 to 6 mg/L, with 3 to 5 mg/L being typical at the beginning of the bathing periods. The bacterial counts are summarized in Table II.

TABLE II

| Day | CFU/mL Before Bathing | CFU/mL After Bathing |
|---|---|---|
| 1 | 5 | 2 |
| 2 | <1 | <1 |
| 6 | >20 | 17 |
| 7 | 5 | 6 |
| 8 | <1 | <1 |
| 9 | <1 | no sample taken |
| 12 | <1 | <1 |
| 13 | 3 | <1 |
| 14 | <1 | no sample taken |
| 15 | <1 | <1 |
| 16 | 2 | no sample taken |
| 19 | 3 | 2 |

EXAMPLE 5

$CaCl_2$ and $NaHCO_3$ were added to three separate 1 L flasks of distilled water to balance the water. A composition of 2.5 g of 2 wt % $Ag/Al_2O_3$ and 2.5 g of Zn shot (formulated as 0.125 in. thick×0.25 in. diameter discs) were added to two of the flasks and allowed to sit for 48 hours. Nothing was added to a third flask of water which served as a control. The effect of the system on alkalinity and calcium hardness of the water is shown in Table III.

TABLE III

| Flask | Initial Alkalinity (mg/L) | Final Alkalinity (mg/L) | Initial Calcium Hardness (mg/L) | Final Calcium Hardness (mg/L) | Initial $[Ag^+]$ (mg/L) | Final $[Ag^+]$ (mg/L) |
|---|---|---|---|---|---|---|
| 1 | 140 | 140 | 150 | 150 | <0.01 | 0.019 |
| 2 | 150 | 135 | 160 | 150 | <0.01 | 0.015 |
| 3 (control) | 140 | 140 | 160 | 160 | <0.01 | <0.01 |

EXAMPLE 6

Nine metals were tested for reduction by the system which consisted of 20 g of 2 wt % $Ag/Al_2O_3$ and 20 g of Zn shot (2–14 mesh) in 500 mL of distilled water. Initial and final concentrations of metal ions were determined by atomic absorption spectroscopy. Table IV shows the metals tested and the reduction in concentration after three days.

| Metal Ion | Initial Concentration (mg/L) | Final Concentration (mg/L) | Percent Reduction |
|---|---|---|---|
| Arsenic | 0.6 | 0.09 | 85 |
| Cadmium | 0.7 | 0.16 | 77 |
| Chromium | 0.6 | <0.05 | >92 |
| Copper | 0.6 | 0.05 | 92 |
| Iron | 0.9 | <0.1 | >89 |
| Lead | 1.0 | <0.05 | >95 |
| Manganese | 0.7 | <0.3 | >57 |
| Mercury | 1.2 | 0.29 | 76 |
| Nickel | 0.8 | <0.4 | >55 |

EXAMPLE 7

A 350 gallon spa contained a cartridge with 50 g of 2 wt % $Ag/Al_2O_3$ and 50 g of Zn shot (2–14 mesh) inside the core of the filter. The spa contained balanced tap water with pH=7.4, total alkalinity=50 mg/L, calcium hardness=110 mg/L as $CaCO_3$, temperature=40° C., $[Ag^+]$=0.08 mg/L, $[Zn^{2+}]$=0.18 mg/L. The system in the presence of 2.0 ppm monopersulfate (in chlorine equivalent units) was tested for its disinfection efficacy against E. coli (ATCC 14948). The flow rate through the system was 2 gallons per minute per gram of purification material for the first minute and 1 gallon per minute per gram of purification material thereafter. The inoculum was prepared by growing cells in Lauria Broth for 24 hours at 37° C. Inoculum was added to the spa at a concentration of approximately $6.3×10^5$ CFU/100 mL. Samples were taken 0.5, 1.0, 1.5, 2.0, 2.5, 3.0, and 5.0 minutes after inoculation and immediately neutralized with 0.2 mL Deox (Taylor Technologies R-0867) and 1.0 mL of a 10% sodium thioglycolate/14.6% sodium thiosulfate solution. Samples were analyzed to determine the number of remaining viable cells (shown in Table V) using serial dilutions and the spread plate method on Tryptic Soy agar and the membrane filtration method (Standard Methods, 9215D).

TABLE V

| Time (min) | Log CFU remaining/100 mL |
|---|---|
| 0.0 | 5.80 |
| 0.5 | 5.18 |
| 1.0 | 5.03 |
| 1.5 | 4.57 |
| 2.0 | 4.26 |
| 2.5 | 3.41 |
| 3.0 | 2.82 |
| 5.0 | 1.49 |

EXAMPLE 8

A cartridge containing 50 g of 2 wt % $Ag/Al_2O_3$ and 50 g of Zn shot (2–14 mesh) was tested by Herbert V. Shuster Laboratories (Quincy, Mass.) using the ANSI/NSF 50-1992 disinfection protocol. The ANSI/NSF 50 standard covers circulating system components, treatment devices, and related materials for use with swimming pools, spas, or hot tubs. The test used 58 gallons of Quincy, Mass. tap water balanced to 100 mg/L alkalinity, 140 mg/L calcium hardness as $CaCO_3$, pH=7.4, 37° C. The water contained $[Ag^+]$=0.03 mg/L. The challenge materials were 4.18 g Lander's baby oil, 1.77 g urea, $2×10^6$ CFU/mL P. aeruginosa, and $2.2×10^6$ CFU/mL E. faecium. Chlorine bleach was delivered to the drum following the ANSI/NSF protocol where residual chlorine levels were 0.3 mg/L after 10 minutes and 0.2 mg/L after 15 minutes. Within two minutes, E. faecium and P. aeruginosa were reduced to less than one organism/mL. The media-containing cartridge in conjunction with 0.2–0.3 mg/L chlorine was effective in disinfection of the test water within the acceptance criteria of ANSI/NSF 50-1992.

EXAMPLE 9

A test of the performance of the system in conjunction with non-halogen oxidizers was performed by Herbert V. Shuster Laboratories (Quincy, Mass.) where the ANSI/NSF 50-1992 protocol was modified such that non-halogen oxidizers were added prior to the test in lieu of chlorine. Three 3000 mL samples of Quincy, Mass. tap water were balanced to 100 mg/L alkalinity, 140 mg/L calcium hardness as $CaCO_3$, and pH=7.4. The water contained $[Ag^+]$=0.06 mg/L. Three oxidizer solutions were tested: monopersulfate alone, hydrogen peroxide alone, and a combination of monopersulfate and hydrogen peroxide. The solutions with monopersulfate were prepared from monopersulfates and contained 3.8 mg/L monopersulfate (in chlorine equivalent units) and the solutions with hydrogen peroxide were prepared from 27% hydrogen peroxide and contained 30 mg/L $H_2O_2$. The solutions were challenged with 27 mg Lander's baby oil, 30 mg urea, $1 \times 10^6$ CFU/mL *P. aeruginosa*, and $1 \times 10^6$ CFU/mL *E. faecium*. The data show that the media-containing cartridge in conjunction with either (1) 3.8 mg/L monopersulfate, (2) 30 mg/L $H_2O_2$ or (3) 3.8 mg/L monopersulfate+30 mg/L $H_2O_2$ exceeded the 3 logarithmic unit reduction of *P. aeruginosa* and the 6 logarithmic unit reduction of *E. faecium* required by ANSI/NSF 50-1992.

EXAMPLE 10

For this example, silver impregnated alumina was made as follows. First, 1 kg of 3/16" alumina sold under the trade designation F-200, manufactured by the Alcoa Corporation of Pittsburgh, Penn., was placed into a rotating drum. Next, 47.6 kg of ACS reagent grade $AgNO_3$, manufactured by Fisher Scientific UK, Bishop Meadow Road, Loughborough, Leica, LE 11 5RG, United Kingdom, were dissolved in 350 mL of distilled water and poured over the alumina with mixing. The media was mixed for 5 minutes, placed into pans, and dried at 250° for 4 hours.

4.4 g of D-glucose were dissolved in 200 mL of tap water. After drying, the D-glucose solution was poured over the silver coated media and mixed for 20 minutes. Afterwards, the media was removed, and dried at approximately 125° F. for 16 hours. After drying, the glucose treated media was heated to 1650° F. for 9 minutes in a reducing atmosphere of $NH_3$ and $N_2$ between about 300° C. and about 1050° C.

Five liters of a balanced water solution were prepared by adding 8.8 g of ACS reagent grade $Ca(NO_3)_2 \cdot 4H_2O$ manufactured by Sigma-Aldrich Corporation, 1001 West Saint Paul Avenue, Milwaukee, Wis. 53233, and 0.69 g of ACS reagent grade $NaHCO_3$ manufactured by Sigma-Aldrich Corporation, 1001 West Saint Paul Avenue, Milwaukee, Wis. 53233, to 5 liters of a type 1 distilled water. Next, one liter portions of the solution were placed into five, 1 liter, Erlenmeyer flasks labeled Flasks A–E.

After allowing the silver impregnated media to cool, 0.5 g of the media was placed into each of the Flasks A and B. One gram of at least about 99 percent pure aluminum dust, manufactured by Sigma-Aldrich Corporation, 1001 West Saint Paul Avenue, Milwaukee, Wis. 53233, was also placed into Flask B. Eight milligrams of ACS reagent grade $AgNO_3$, manufactured by Fisher Scientific UK, Bishop Meadow Road, Loughborough, Leica, LE 11 5RG, United Kingdom, were added to each of the Flasks C and D. One gram of aluminum dust, same purity as added to Flask B, was also added to Flask D. Flask E was designated as a control flask and no additions were made. Solutions were covered to prevent evaporation and left to sit at a room temperature of 22° C. Each solution was checked for silver ion concentrations at 5, 10, 15, and 20 days as follows: the pH of each solution was adjusted to between 7.4 and 7.8 immediately before analysis using 1 M $HNO_3$, and a 50 mL aliquot of each solution was filtered through a 0.45 micron TEFLON filter and tested for free silver by the colorimetric method using a HACH DR4000 spectrophotometer.

The results of these test depicted below in Table VI.

TABLE VI

| Speci-men | Flask | Contents Added | Silver Ion (ppm) Level of Test Solutions | | | |
|---|---|---|---|---|---|---|
| | | | 5 days | 10 days | 15 days | 20 days |
| 1 | A | 0.5 g Ag Media | 2.43 | 2.84 | 3.07 | 3.18 |
| 2 | B | 0.5 g Ag Media/ 1 g Al dust | 0.035 | 0.029 | 0.022 | 0.022 |
| 3 | C | 8 mg $AgNO_3$ | 6.13 | 6.08 | 5.87 | 6.01 |
| 4 | D | 8 mg $AgNO_3$/ 1 g Al dust | 0.018 | 0.007 | <0.006 | <0.006 |
| 5 | E | Nothing | <0.006 | <0.006 | <0.006 | <0.006 |

As depicted by Table VI, the combination of the silver media plus the aluminum dust yielded a silver ion concentration of between about 0.01 to about 0.1 parts per million for 20 days. This combination yielded superior silver concentrations over time as compared to the other test compositions.

EXAMPLE 11

In this example, silver ion levels were compared between two test solutions. One test solution only used the silver impregnated alumina, while the other used the silver impregnated alumina along with aluminum dust.

For this example, silver impregnated alumina was made as follows. First, 1 kg of 3/16" alumina sold under the trade designation F-200 by Alcoa Corporation was placed into a rotating drum. Next, 95.2 kg of ACS reagent grade $AgNO_3$, manufactured by Fisher Scientific UK, Bishop Meadow Road, Loughborough, Leica, LE 11 5RG, United Kingdom were dissolved in 350 mL of distilled water and poured over the alumina with mixing. The media was mixed for 5 minutes, placed into pans, and dried at 250° F. for 4 hours.

Meanwhile, 4.4 g of D-glucose were dissolved in 200 mL of tap water. After drying, the D-glucose solution was poured over the silver coated media and mixed for 20 minutes. Afterwards, the media was removed, and dried at approximately 125° F. for 16 hours. After drying, the glucose treated media was heated to 1650° F. for 9 minutes in a reducing atmosphere of $NH_3$ and $N_2$ between about 300° C. and about 1050° C.

Three liters of a balanced water solution were prepared by adding 5.3 g of ACS reagent grade $Ca(NO_3)_2 \cdot 4H_2O$ manufactured by Sigma-Aldrich Corporation, 1001 West Saint Paul Avenue, Milwaukee, Wis. 53233 and 0.42 g of ACS reagent grade $NaHCO_3$ manufactured by Sigma-Aldrich Corporation, 1001 West Saint Paul Avenue, Milwaukee, Wis. 53233, to 3 liters of a type 1 distilled water. Next one liter portions of the solution was placed into three, 1 liter, Erlenmeyer flasks labeled Flasks A–C.

After cooling, 1 gram of the silver impregnated media was placed into each of the Flasks A and B. In addition, 1 gram of at least about 99 percent pure aluminum dust manufactured by Sigma-Aldrich Corporation, 1001 West Saint Paul Avenue, Milwaukee, Wis. 53233 was also placed into Flask B. The control was Flask C, consequently, no additions were made to it. The solutions were covered to prevent evaporation and left to sit at room temperature of 22° C. Each solution was checked for silver ion concentration at 5, 10, 15, 20, 25, 30, and 35 days. Prior to measuring the silver ion concentration, the pH of each solution was adjusted to between 7.4 and 7.8 immediately before analysis using a 1M $HNO_3$. In addition, a 50 mL aliquot of each solution was filtered through a 0.45 micron TEFLON filter. The solution was tested for free silver by the calorimetric method using a HACH DR4000 spectrophotometer.

The results of the silver ion concentration are depicted below in Table VII.

TABLE VII

| | | | Silver Ion (ppm) Level of Test Solutions | | | | | |
| --- | --- | --- | --- | --- | --- | --- | --- | --- |
| Specimen | Flask | Contents Added | 5 days | 10 days | 15 days | 20 days | 25 days | 30 days | 35 days |
| 1 | A | 1.0 g Ag Media | 7.26 | 12.5 | 14.8 | 15.8 | 16.2 | 15.6 | 16.0 |
| 2 | B | 1.0 g Ag Media/ 1 g Al dust | 1.16 | 0.84 | 0.17 | 0.027 | 0.019 | 0.019 | 0.024 |
| 3 | C | Nothing | <0.006 | <0.006 | <0.006 | <0.006 | <0.006 | <0.006 | <0.006 |

Table VII illustrates that the combination of silver media and aluminum dust results in a desired silver ion concentration between 0.01 and 0.1 ppm after 20 days. Consequently, this combination should extend the desired silver ion concentration for killing bacteria.

Other embodiments of the present invention not specifically exemplified above are within the scope of the claims. For example, the elemental silver may be added as a powder, shavings or turnings rather than being chemically deposited on the support medium. Further, the support material of the water purification composition can include other ceramic or ceramic foam materials, such as silicon carbide foams. Even further, it has been discovered that the silver ion concentration may be further affected by various factors that have an effect on other equilibria occurring in the solution. For example, silver ion concentration generally increases with increasing temperature, with decreasing silver particle size, with increasing specific surface area of the second metal, and with increasing oxidation-reduction potential or ORP (which can be affected by pH and/or oxidizer concentration).

The present invention having been thus described, it will be understood that variations and modifications thereto can be made without departing from the spirit and scope of the invention. These variations are intended to be within the scope of the appended claims, or of equivalents thereto.

What is claimed is:

1. A method of purifying water comprising exposing the water to an effective amount of a water purification composition comprising silver and aluminum metal.

2. The method of claim 1, wherein the water purification composition further comprises zinc, copper, or mixtures thereof.

3. The method of claim 1, wherein the silver is metallic silver.

4. The method of claim 2, wherein the aluminum is alloyed with zinc, copper, or both.

5. The method of claim 1, wherein the water purification composition further comprises an inorganic oxide having a point of zero charge between about 4 and about 9.

6. The method of claim 5, wherein the inorganic oxide has a zeta potential less than or equal to about +20 mV in water having a pH of about 5.0 to about 10.

7. The method of claim 5, wherein the inorganic oxide comprises alumina.

8. The method of claim 1, wherein the silver comprises between about 0.1 and about 10 weight percent of the water purification composition.

9. The method of claim 1, wherein the aluminum metal comprises between about 2 and about 95 weight percent of the water purification composition.

10. The method of claim 1, wherein the water purification composition provides a silver ion concentration in water between about 0.01 and about 0.1 ppm when exposed to the water.

11. The method of claim 10, wherein the water purification composition provides a silver ion concentration in water between about 0.01 and about 0.05 ppm when exposed to the water.

12. The method of claim 1, wherein the silver is a source of microbiocidal silver ions in the water and the aluminum flocculates suspended material in the water.

13. The method of claim 1, wherein the composition further comprises zinc or copper.

14. The method of claim 1, wherein the composition further comprises an inorganic oxide having a zeta potential less than or equal to about +20 mV in the water being purified.

15. The method of claim 1, wherein the water is recirculated.

16. The method of claim 1, wherein the water is drinking water.

17. The method of claim 1, wherein the water comprises an oxidizing agent dissolved in the water.

18. The method of claim 14, wherein the inorganic oxide comprises alumina.

19. The method of claim 1, wherein the silver in the composition comprises silver metal in an amount between about 0.1 and about 10 weight percent of the composition.

20. The method of claim 17, wherein the oxidizing agent comprises ozone, chlorine dioxide or free available chlorine.

21. A water purification system comprising:

a water purification composition comprising silver and aluminum metal; and an oxidizing agent or a source of an oxidizing agent.

22. The water purification system of claim 21, wherein the silver is metallic silver.

23. The water purification system of claim 21, wherein the aluminum metal is alloyed with at least one metal selected from the group consisting of zinc metal and copper metal.

24. The water purification system of claim 21, wherein the oxidizing agent is selected from the group consisting of free available chlorine, ozone, and chlorine dioxide.

25. The water purification system of claim 21, wherein the source of oxidizing agent is selected from the group consisting of dipersulfates, monopersulfates, hypochlorite salts, chlorites, peroxides, perchlorates, hypobromites, percarbonates, chlorine dioxide and permanganates.

* * * * *